United States Patent
Carrazana et al.

(10) Patent No.: US 6,319,903 B1
(45) Date of Patent: Nov. 20, 2001

(54) ANTICONVULSANT DERIVATIVES USEFUL IN TREATING CLUSTER HEADACHES

(75) Inventors: Enrique J. Carrazana, Key Biscayne; Steve D. Wheeler, Miami, both of FL (US)

(73) Assignee: Ortho-McNeil Pharmaceutical, Inc., Skillman, NJ (US)

( * ) Notice: Subject to any disclaimer, the term of this patent is extended or adjusted under 35 U.S.C. 154(b) by 0 days.

(21) Appl. No.: 09/482,801

(22) Filed: Jan. 13, 2000

Related U.S. Application Data

(60) Provisional application No. 60/116,388, filed on Jan. 19, 1999.

(51) Int. Cl.[7] .................................................. A61K 31/70
(52) U.S. Cl. .............................. 514/23; 514/459; 514/517
(58) Field of Search ................................ 514/23, 459, 577

(56) References Cited

U.S. PATENT DOCUMENTS 4,513,006 * 4/1985 Maryanoff et al. .
5,998,380 * 12/1999 Ehrenberg et al. ..................... 514/23

FOREIGN PATENT DOCUMENTS

9713510A * 4/1997 (WO) .
98152270A * 4/1998 (WO) .

OTHER PUBLICATIONS

Kuziesky et al "Topiramate increases cerebral GABA in healthy humans", Neurology (Aug. 1998) 51 (2) 627–9.*
Hering et al "Sodium valproate in the treatment of cluster headache" Cephalalgia (Sep. 1989) 9 (3) 195–8.*
Wheeler, "Significance of migrainous features in cluster headache". Headache. (1998). 38/7. (547–551).*
Wheeler et al "Topiramate–treated cluster headache". Neurology (Jul. 1999) vol. 53. No. 1 pp. 234–236.*
The Merck Manual (1987), Merck Sharp & Dohme Research Laboratories, Rahway, NJ, XP002144176, pp. 1351–1356.

* cited by examiner

Primary Examiner—Elli Peselev
(74) Attorney, Agent, or Firm—Mary Appollina

(57) ABSTRACT

Anticonvulsant derivatives useful in treating cluster headaches are disclosed.

15 Claims, No Drawings

ANTICONVULSANT DERIVATIVES USEFUL IN TREATING CLUSTER HEADACHES

CROSS-REFERENCE TO RELATED APPLICATION

This application claims priority from U.S. provisional application Serial No. 60/116,388, filed Jan. 19, 1999, the contents of which are hereby incorporated by reference.

BACKGROUND OF THE INVENTION

Compounds of Formula I:

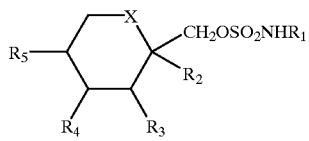

are structurally novel antiepileptic compounds that are highly effective anticonvulsants in animal tests (Maryanoff, B. E, Nortey, S. O., Gardocki, J. F., Shank, R. P. and Dodgson, S. P. *J Med. Chem.* 30, 880–887, 1987; Maryanoff, B. E., Costanzo, M. J., Shank, R. P., Schupsky, J. J., Ortegon, M. E., and Vaught J. L. Bioorganic & Medicinal Chemistry Letters 3, 2653–2656, 1993). These compounds are covered by U.S. Pat. No.4,513,006. One of these compounds 2,3:4,5-bis-O-(1-methylethylidene)-β-D-fructopyranose sulfamate known as topiramate has been demonstrated in clinical trials of human epilepsy to be effective as adjunctive therapy or as monotherapy in treating simple and complex partial seizures and secondarily generalized seizures (E. FAUGHT, B. J. WILDER, R. E. RAMSEY, R. A. REIFE, L D. KRAMER, G. W. PLEDGER, R. M. KARIM et. al., Epilepsia 36 (S4) 33, 1995; S. K. SACHDEO, R. C. SACHDEO, R. A. REIFE, P. LIM and G. PLEDGER, Epilepsia 36 (S4) 33, 1995), and is currently marketed for the treatment of simple and complex partial seizure epilepsy with or without secondary generalized seizures in approximately twenty countries including the United States, and applications for regulatory approval are presently pending in several additional countries throughout the world.

Compounds of Formula I were initially found to possess anticonvulsant activity in the traditional maximal electroshock seizure (MES) test in mice (SHANK, R. P., GARDOCKI, J. F., VAUGHT, J. L., DAVIS, C. B., SCHUPSKY, J. J., RAFFA, R. B., DODGSON, S. J., NORTEY, S. O., and MARYANOFF, B. E., Epilepsia 35 450–460, 1994). Subsequent studies revealed that Compounds of Formula I were also highly effective in the MES test in rats. More recently topiramate was found to effectively block seizures in several rodent models of epilepsy (J. NAKAMURA, S. TAMURA, T. KANDA, A. ISHII, K. ISHIHARA, T. SERIKAWA, J. YAMADA, and M. SASA, Eur. J. Pharmacol. 254 83–89, 1994), and in an animal model of kindled epilepsy (A. WAUQUIER and S. ZHOU, Epilepsy Res. 24, 73–77, 1996).

Cluster headache is an excruciating painful disorder associated with considerable suffering which is characterized by severe, short duration, unilateral orbital-temporal pain, Ipsilateral autonomic dysfunction and chronobiological disturbances. (A. Kudrow, The pathogenesis of a cluster headache, Curr. Opin. Neurol. 7:278–282, 1994; Headache Classification Committee of the International Headache Society, Classification and diagnostic criteria for headache disorders, cranial neuralgias and facial pain, Cephalgia S7:1–96, 1988). Although treatment is often successful, some patients have intractable pain. Thus, a need remains for effective treatments for cluster headaches.

Studies on five patients treated with topiramate have revealed previously unrecognized pharmacological properties which suggest that topiramate is effective in treating cluster headaches.

DISCLOSURE OF THE INVENTION

Accordingly, it has been found that compounds of the following formula I:

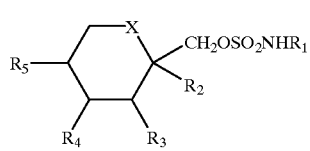

wherein X is O or $CH_2$, and R1, R2, R3, R4 and R5 are as defined hereinafter are useful in treating cluster headaches.

DETAILED DESCRIPTION OF THE PREFERRED EMBODIMENTS

The sulfamates of the invention are of the following formula (I):

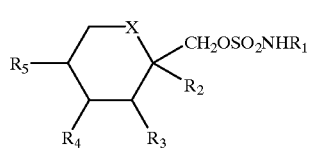

wherein
X is $CH_2$ or oxygen;
$R_1$ is hydrogen or $C_1$–$C_4$ alkyl; and
$R_2$, $R_3$, $R_4$ and $R_5$ are independently hydrogen or $C_1$–$C_3$ alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

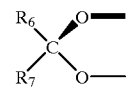

wherein
$R_6$ and $R_7$ are the same or different and are hydrogen, $C_1$–$C_3$ alkyl or are alkyl and are joined to form a cyclopentyl or cyclohexyl ring.

$R_1$ in particular is hydrogen or alkyl of about 1 to 4 carbons, such as methyl, ethyl, iso-propyl, n-propyl, n-butyl, isobutyl, sec-butyl and t-butyl. Alkyl throughout this specification includes straight and branched chain alkyl. Alkyl groups for $R_2$, $R_3$, $R_4$, $R_5$, $R_6$ and $R_7$ are of about 1 to 3 carbons and include methyl, ethyl, iso-propyl and n-propyl. When X is $CH_2$, $R_4$ and $R_5$ may combine to form a benzene ring fused to the 6-membered X-containing ring, i.e., $R_4$ and $R_5$ are defined by the alkatrienyl group =C—CH=CH—CH=.

A particular group of compounds of formula (I) is that wherein X is oxygen and both $R_2$ and $R_3$ and $R_4$ and $R_5$ together are methylenedioxy groups of the formula (II), wherein $R_6$ and $R_7$ are both hydrogen both alkyl or combine to form a spiro cyclopentyl or cyclohexyl ring, in particular where $R_6$ and $R_7$ are both alkyl such as methyl. A second group of compounds is that wherein X is $CH_2$ and $R_4$ and $R_5$ are joined to form a benzene ring. A third group of compounds of formula (I) is that wherein both $R_2$ and $R_3$ are hydrogen.

A particularly preferred compound for use in the methods of the present invention is 2,3 :4,5-bis-O-(1-methylethylidene)-β-D-fructopyranose sulfamate, known as topiramate. Topiramate has the following structural formula

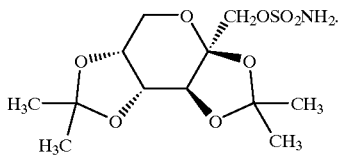

The compounds of formula (I) may be synthesized by the following methods:

(a) Reaction of an alcohol of the formula $RCH_2OH$ with a chlorosulfamate of the formula $ClSO_2NH_2$ or $ClSO_2NHR_1$ in the presence of a base such as potassium a-butoxide or sodium hydride at a temperature of about −20° to 25° C. and in a solvent such as toluene, THF or dimethylformamide wherein R is a moiety of the following formula (III):

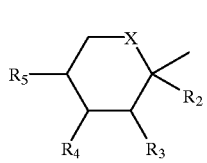

(b) Reaction of an alcohol of the formula $RCH_2OH$ with sulfurylchloride of the formula $SO_2Cl_2$ in the presence of a base such as triethylamine or pyridine at a temperature of about −40° to 25° C. in a solvent such as diethyl ether or methylene chloride to produce a chlorosulfate of the formula $RCH_2OSO_2Cl$.

The chlorosulfate of the formula $RCH_2OSO_2Cl$ may then be reacted with an amine of the formula $R_1NH_2$ at a temperature of abut 40° to 25° C. in a solvent such as methylene chloride or acetonitrile to produce a compound of formula (I). The reaction conditions for (b) are also described by T. Tsuchiya et al. in Tet. Letters, No. 36, p. 3365 to 3368 (1978).

(c) Reaction of the chlorosulfate $RCH_2OSO_2Cl$ with a metal azide such as sodium azide in a solvent such as methylene chloride or acetonitrile yields an azidosulfate of the formula $RCH_2OSO2N_3$ as described by M. Hedayatullah in Tet. Lett. p. 2455–2458 (1975). The azidosulfate is then reduced to a compound of formula (I) wherein $R_1$ is hydrogen by catalytic hydrogenation, e.g. with a noble metal and $H_2$ or by heating with copper metal in a solvent such as methanol.

The starting materials of the formula $RCH_2OH$ may be obtained commercially or as known in the art. For example, starting materials of the formula $RCH_2OH$ wherein both $R_2$ and $R_3$ and $R_4$ and $R_5$ are identical and are of the formula (II) may be obtained by the method of R. F. Brady in Carbohydrate Research, Vol. 14, p. 35 to 40 (1970) or by reaction of the trimethylsilyl enol ether of a $R_6COR_7$ ketone or aldehyde with fructose at a temperature of about 25° C., in a solvent such a halocarbon, e.g. methylene chloride in the presence of a protic acid such as hydrochloric acid or a Lewis Acid such as zinc chloride. The trimethylsilyl enol ether reaction is described by G. L. Larson et al in J. Org. Chem. Volaa 38, No. 22, p. 3935 (1973).

Further, carboxylic acids and aldehydes of the formulae RCOOH and RCHO may be reduced to compounds of the formula $RCH2OH$ by standard reduction techniques, e.g. reaction with lithium aluminum hydride, sodium borohydride or borane-THF complex in an inert solvent such a diglyme, THF or toluene at a temperature of about 0° to 100° C., e.g. as described by H.O. House in "Modem Synthetic Reactions", 2nd Ed., pages 45 to 144 (1972).

The compounds of formula I: may also be made by the processes disclosed in U.S. Pat. Nos. 4,513,006, 5,387,700 and 5,387,700, all of which are incorporated herein by reference. More particularly, topiramate may be prepared following the process described in Examples 1 to 3 of U.S. Pat. No. 5,387,700.

The compounds of formula I include the various individual isomers as well as the racemates thereof, e.g., the various alpha and beta attachments, i.e., below and above the plane of the drawing, of $R_2$, $R_3$, $R_4$ and $R_5$ on the 6-membered ring. Preferably, the oxygen of the methylenedioxy group (II) are attached on the same side of the 6-membered ring.

The term "subject" as used herein, refers to an animal, preferably a mammal, most preferably a human, who has been the object of treatment, observation or experiment.

The term "therapeutically effective arnount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The activity of the compounds of formula I in treating cluster headaches was evidenced in experimental research studies of five patients as indicated in the examples which follow.

For treating cluster headaches, a compound of formula (I) may be employed at a daily dosage in the range of about 15 to 1000 mg, preferably, about 25 mg to about 400 mg, most preferably, about 25 mg to about 200 mg, administered one to four times per day, preferably, one to two times per day, for an average adult human. A unit dose typically contains about 25 to 200 mg of the active ingredient.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable solutions may also be prepared in which case appropriate stabilizing agents may be employed. Topiramate is currently available for oral administration in round tablets containing 25 mg, 100 mg or 200 mg of active agent. The tablets contain the following inactive ingredients: lactose hydrous, pregelatinized starch, microcrystalline cellulose, sodium starch glycolate, magnesium stearate, purified water, camauba wax, hydroxypropyl methylcellulose, titanium dioxide, polyethylene glycol, synthetic iron oxide, and polysorbate 80.

The pharmaceutical compositions herein will contain, per dosage unit, e.g., tablet, capsule, powder injection, teaspoonful, suppository and the like from about 25 to about 200 mg of the active ingredient.

The following Examples are set forth to aid in the understanding of the invention, and are not intended and should not be construed to limit in any way the invention set forth in the claims which follow thereafter.

EXAMPLE 1

A 50-year-old male had cluster headache since age fourteen. Severe right retro-orbital pain accompanied ipsilateral lacrimation, conjunctive injection, nasal congestion and rhinorrhea. Attacks last 30 minutes to two hours and occur three to five times daily. The cluster period usually lasts two to three months when topiramate started and resolved within three weeks of starting 25 mg twice daily. Subsequently, he has been noncompliant with topiramate. He will take 25 mg daily when cluster attacks return. Controlling headaches in three to four days, then stopping the medication.

EXAMPLE 2

A 42-year-old male had cluster headaches since age ten. Severe right oribital-frontal pain accompanied ipsilateral nasal congestion, rhinorrhea, ptosis, conjunctival injection, and lacrimation. Attacks last 15 to 60 minutes. The cluster period typically lasts four to eight weeks and the last occurred one and a half years ago. The first topiramate treated cluster period had been present for three months when topiramate was begun and resolved within one week of starting 50 mg daily. After topiramate taper there has been no recurrance in seven months. Verapamil, gabapentin and valproate had failed.

EXAMPLE 3

A 51-year-old male had cluster headaches since age 45. Severe left orbital-temporal pain accompanied ipsilateral rhinorrhea and ptosis. The attacks last 15 to 30 minutes and occur one to five times daily. Typically the cluster period lasts three to four months and the last cluster period ended three months ago. The first topiramate treated cluster period had been present for one month when he started topiramate and resolved within one week of starting 50 mg twice daily.

EXAMPLE 4

A 27-year-old male had cluster headaches since age 17. Severe left orbital-temporal pain accompanied ipsilateral lacrimation and nasal congestion. The attacks last 15 to 180 minutes and occur sporadically and in clusters. Typically the cluster period lasts two to four months and the last cluster period occurred two years ago. He experiences one to four headaches daily. The first topiramate treated cluster period had been present for one month when he started topiramate; resolved within three weeks at a peak dose of 125 mg daily. Verapamil, valproate, methysergide and gabapentin had failed.

EXAMPLE 5

A 72-year-old male had cluster headaches since age 59. Severe right orbital-temporal pain accompanied ipsilateral lacrimation, conjunctival injection, eye lid edema, and nasal congestion. The attacks last 20 to 90 minutes and occur one to two times daily. Usually the cluster period lasts two to four months, once as long as 12 months. The last cluster period occurred two years ago, although sporadic attacks occurred. The first topiramate treated cluster period had been present for 10 months and nearly controlled with daily methylprednisolone for one month when topiramate was started. On topiramate 100 mg daily he remained headache free and methylprednisolone tapered without recurrence. Verapamil and valproate had failed.

Topiramate produced rapid improvement in the induction of cluster remission and reduction in cluster period duration in the five patients studied with episodic cluster headaches. Moreover, all five patients responded at relatively low doses and no major side effects were reported.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method for treating cluster headaches in a subject in need thereof comprising administering to the subject a therapeutically effective amount of a compound of the formula I:

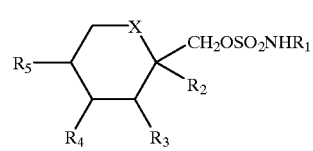

wherein

X is oxygen;

$R_1$ is hydrogen or $C_1$–$C_4$ alkyl; and $R_2$, $R_3$, $R_4$ and $R_5$ are independently hydrogen or $C_1$–$C_3$ alkyl; or $R_2$ and $R_3$ and/or $R_4$ and $R_5$ together may be a methylenedioxy group of the following formula (II):

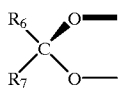

wherein $R_6$ and $R_7$ are the same or different and are hydrogen, $C_1$–$C_3$ alkyl or $R_6$ and $R_7$ together with the carbon to which they are attached are joined to form a cyclopentyl or cyclohexyl ring.

2. The method of claim 1, wherein the compound of formula I is topiramate.

3. The method of claim 1, wherein the therapeutically effective amount is from about 15 mg to about 1000 mg.

4. The method of claim 1, wherein the therapeutically effective amount is from about 25 mg to about 200 mg.

5. The method of claim 1, wherein the compound is administered as a pharmaceutical composition.

6. A method of inducing cluster remission in a subject suffering from cluster headaches comprising administering to the subject a therapeutically effective amount of a compound of the formula I:

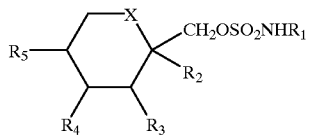

wherein

X is oxygen;

$R_1$ is hydrogen or $C_1$–$C_4$ alkyl; and $R_2$, $R_3$, $R_4$ and $R_5$ are independently hydrogen or $C_1$–$C_3$ alkyl; or $R_2$ and $R_3$ and/or $R_4$ and $R_5$ together may be a methylenedioxy group of the following formula (II):

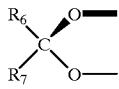

wherein $R_6$ and $R_7$ are the same or different and are hydrogen, $C_1$–$C_3$ alkyl or $R_6$ and $R_7$ together with the carbon to which they are attached are joined to form a cyclopentyl or cyclohexyl ring.

7. The method of claim 6, wherein the compound of formula I is topiramate.

8. The method of claim 6, wherein the therapeutically effective amount is from about 15 mg to about 1000 mg.

9. The method of claim 6, wherein the therapeutically effective amount is from about 25 mg to about 200 mg.

10. The method of claim 6, wherein the compound is administered as a pharmaceutical composition.

11. A method of reducing cluster period duration in a subject suffering from cluster headaches comprising administering to the subject a therapeutically effective amount of a compound of the formula I:

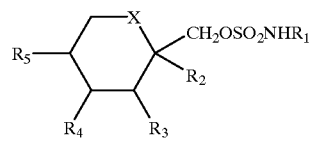

wherein

X is oxygen;

$R_1$ is hydrogen or $C_1$–$C_4$ alkyl; and $R_2$, $R_3$, $R_4$ and $R_5$ are independently hydrogen or $C_1$–$C_3$ alkyl; or $R_2$ and $R_3$ and/or $R_4$ and $R_5$ together may be a methylenedioxy group of the following formula (II):

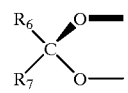

wherein $R_6$ and $R_7$ are the same or different and are hydrogen, $C_1$–$C_3$ alkyl or $R_6$ and $R_7$ together with the carbon to which they are attached are joined to form a cyclopentyl or cyclohexyl ring.

12. The method of claim 11, wherein the compound of formula I is topiramate.

13. The method of claim 11, wherein the therapeutically effective amount is from about 15 mg to about 1000 mg.

14. The method of claim 11, wherein the therapeutically effective amount is from about 15 mg to about 200 mg.

15. The method of claim 11, wherein the compound is administered as a pharmaceutical composition.

* * * * *